United States Patent
Pennemann et al.

(10) Patent No.: US 11,231,727 B2
(45) Date of Patent: *Jan. 25, 2022

(54) METHOD FOR CONTINUOUSLY PRODUCING A PRODUCT BY WAY OF AT LEAST TWO COUPLED-TOGETHER CHEMICAL REACTIONS

(71) Applicant: Covestro Deutschland AG, Leverkusen (DE)

(72) Inventors: Bernd Pennemann, Bergisch Gladbach (DE); Erwin Dieterich, Cologne (DE); Heinz-Josef Hamacher, Bedburg (DE)

(73) Assignee: Covestro Deutschland AG, Leverkusen (DE)

( * ) Notice: Subject to any disclaimer, the term of this patent is extended or adjusted under 35 U.S.C. 154(b) by 44 days.

This patent is subject to a terminal disclaimer.

(21) Appl. No.: 16/878,923

(22) Filed: May 20, 2020

(65) Prior Publication Data

US 2020/0301452 A1    Sep. 24, 2020

Related U.S. Application Data

(62) Division of application No. 15/526,871, filed as application No. PCT/EP2015/076857 on Nov. 17, 2015, now Pat. No. 10,698,424.

(30) Foreign Application Priority Data

Nov. 20, 2014 (EP) .................................. 14194180

(51) Int. Cl.
*G05D 7/06* (2006.01)
*C07C 201/08* (2006.01)
(Continued)

(52) U.S. Cl.
CPC ........ *G05D 7/0623* (2013.01); *B01J 19/0006* (2013.01); *C07C 201/08* (2013.01);
(Continued)

(58) Field of Classification Search
CPC ......... B01J 19/0006; B01J 2219/00191; F16K 31/02; C07C 201/08; C07C 205/06; G05B 11/42; G05D 7/0623
See application file for complete search history.

(56) References Cited

U.S. PATENT DOCUMENTS 4,022,844 A * 5/1977 de Cazenove ........... B01J 19/18
  568/934
5,902,910 A   5/1999 Mazzafro et al.
(Continued)

OTHER PUBLICATIONS

Hermann H. et al.; "Industrial Nitration of Toluene to Dinitrotoluene" in: "Nitration", Chapter 21; Apr. 24, 1996; pp. 234-249; ACS Symposium Series, American Chemical Society, Washington, DC.
(Continued)

*Primary Examiner* — Shogo Sasaki
(74) *Attorney, Agent, or Firm* — Donald R. Palladino; N. Denise Brown

(57) ABSTRACT

A method for continuously producing a product (A1) by way of at least two coupled-together chemical reactions (C1, C2), wherein at least two input substances (E1, E2) are fed to a first chemical reaction (C1), wherein a plurality of intermediate substances (Z1, Z2) are produced from the input substances (E1, E2) by the first chemical reaction (C1), wherein at least one of the intermediate substances (Z2) is fed to a second chemical reaction (C2), wherein the at least one fed intermediate substance (Z2) is further processed by the second chemical reaction (C2), in particular using at least one further substance (W1, W2) in a second chemical reaction (C2) to form a plurality of output substances (A1, A2), that is to say to form the chemical product (A1) and at
(Continued)

least one further output substance (A2), wherein the flow rates ($F_i$) of the fed substances (E1, E2, Z1, W1, W2, A2) that are fed to one of the reactions (C1, C2) are set by a respective actuating element ($V_{E1}$, $V_{E2}$, $V_{W1}$, $V_{W2}$, $V_{Z2}$, $V_{A1}$), wherein each of the fed substances is assigned a separate actuating element, wherein a manipulated variable ($S_{E2,R}$, $S_{i,R}$) that is stipulated by a controller ($R_{E2}$, $R_i$) is respectively applied to at least one of the actuating elements, wherein, for changing the production rate of the chemical product (A1), a temporary manipulated variable ($S_{E2,temp}$, $S_{i,temp}$) is respectively applied during a transient phase (II, III) to at least one of these actuating elements ($V_{E2}$, $V_i$) instead of the manipulated variables ($S_{E2,R}$, $S_{i,R}$) stipulated by the respective controllers ($R_{E2}$, $R_i$), wherein the temporary manipulated variable ($S_{E2,temp}$, $S_{i,temp}$) or the temporary manipulated variables is/are generated by at least one control unit (SE) in dependence on a default value (NV).

11 Claims, 10 Drawing Sheets

(51) Int. Cl.
*B01J 19/00* (2006.01)
*F16K 31/02* (2006.01)
*G05B 11/42* (2006.01)
*C07C 205/06* (2006.01)

(52) U.S. Cl.
CPC ..... *F16K 31/02* (2013.01); *B01J 2219/00191* (2013.01); *C07C 205/06* (2013.01); *G05B 11/42* (2013.01)

(56) References Cited

U.S. PATENT DOCUMENTS

| | | | |
|---|---|---|---|
| 7,041,858 B1* | 5/2006 | Muennig | C07C 201/08 |
| | | | 568/927 |
| 2008/0086017 A1 | 4/2008 | Pohl et al. | |
| 2008/0242900 A1 | 10/2008 | Buttner et al. | |
| 2015/0301522 A1* | 10/2015 | Ochs | B01J 19/004 |
| | | | 700/266 |
| 2016/0299477 A1* | 10/2016 | Krasberg | G05B 13/024 |

OTHER PUBLICATIONS

International Search Report, PCT/EP2015/076857, dated Jan. 14, 2016, Authorized officer: Brigitte Zervas.

\* cited by examiner

METHOD FOR CONTINUOUSLY PRODUCING A PRODUCT BY WAY OF AT LEAST TWO COUPLED-TOGETHER CHEMICAL REACTIONS

CROSS-REFERENCE TO RELATED APPLICATION

The present application is a divisional application of U.S. application Ser. No. 15/526,871, filed on May 15, 2017, now patented as U.S. Pat. No. 10,698,424 B2, and which is a National Phase Application of PCT/EP2015/076857, filed Nov. 17, 2015, which claims priority to European Application No. 14194180.7 filed Nov. 20, 2014, each of which is being incorporated herein by reference.

FIELD

The invention relates to a process for the continuous production of a product via at least two coupled chemical reactions.

BACKGROUND

Many chemical products are produced industrially in processes operated continuously or semicontinuously. Here, one or more starting materials are processed further in a chemical reaction to form other materials. One or more of the materials produced in this way can in turn go into a subsequent second chemical reaction in which the desired end product is finally produced. Here, continuously means that materials are fed without interruption to the chemical reactions and that the chemical reactions produce reaction products (in the subsequent process the starting materials or the intermediates) without interruption. "Without interruption" here refers to the periods of time in which the reaction actually takes place and does not exclude the possibility of a reaction being interrupted, for example as a result of a maintenance shutdown. In the following, the substances fed into the production processes are referred to as starting materials, abbreviated to "E". The products flowing out from the outlet of the plant are referred to as output materials, abbreviated to "A". The intermediates are denoted by "Z" by way of abbreviation.

In such nested processes, coproducts are inevitably also formed because of the prescribed stoichiometry of the underlying reaction equation. In industrial processes, efforts are made for reasons of economics and environmental protection to reuse coproducts formed to the greatest possible extent. For example, hydrogen chloride is obtained as coproduct in many chemical processes such as the preparation of isocyanates by phosgenation of the corresponding amine compounds and can be used again, for example after oxidation to chlorine.

Such coproducts can likewise be formed in multistage reactions, and there are cases in which the coproduct of a subsequent reaction can be fed as starting material to the first chemical reaction, optionally after prior treatment. Such cases include the preparation of dinitrotoluene by a first chemical reaction, viz. the nitration of toluene to form nitrotoluene, followed by a second chemical reaction, viz. the nitration of nitrotoluene to form dinitrotoluene. The nitration is usually carried out by means of a mixture of nitric acid and sulfuric acid, giving an acid phase ("used acid") which is diluted by the coproduct of the nitration, namely water. The second reaction to dinitrotoluene requires a higher sulfuric acid concentration than the first reaction to form nitrotoluene. The concentrated sulfuric acid is therefore usually introduced into this second reaction step, this is separated off after the reaction is complete and sulfuric acid which has been diluted by the reaction is introduced into the first reaction step. Here too, water is formed as coproduct and dilutes the sulfuric acid further. In the first reaction, too, the sulfuric acid is separated off. This is usually concentrated up and can subsequently be used again in the second reaction stage.

Such a process is described below in abstracted form in FIG. 1; the materials Z1 and A2 can be considered to be coproducts since they are obtained in a predetermined particular ratio to one another because of the nature of the reaction which proceeds. The coupling of these two chemical reactions in this way has many economic and ecological advantages since the amount of waste streams obtained is minimized in this mode of operation. However, such coupling of two chemical reactions also presents challenges.

The mass flows of all materials fed to the chemical reactions (hereinafter also referred to in general terms as materials) have to be matched precisely to one another. This has hitherto been achieved by setting down the intended flow rate $F_{i,int}$ or the actual flow rate $F_{i,act}$ of a selected material and regulating the mass flows of the other materials to suitable intended flow rates $F_{i,int}$ relative to this flow rate. The ideal ratio, naturally always within the window determined by the stoichiometry of the underlying reaction equation, of the intended mass flows $F_{i,int}$ of the other materials to the flow rate of the prescribed material is known for all customary chemical reactions from the patent and technical literature and can also be determined by engineering calculations known to those skilled in the art.

In the case of a production plant for coupled reactions, the start-up or the setting of relatively large changes in the intended amount produced per unit time therefore requires particular care. In practice, the procedure is to set down the intended mass flow of a starting material or an output material (in the process shown in FIG. 1, for example the first starting material E1) and increasing this from the instantaneous actual value by an essentially linear increase, with the mass flow being increased only slowly. The intended values of the flow rates of the other materials are then set analogously in relation to the flow rate of the prescribed material.

During a "settling-down process" (which will also be explained below with the aid of FIG. 9), more or less large deviations of the actual values from the intended values of the flow rates are unavoidable. Since many mass flows have to be matched to one another in production processes having coupled reactions, the risk of undesirable deviations which in the extreme case could lead to interruption of the process is particularly great. This also applies particularly because increases in the mass flows have hitherto been carried out slowly, namely in many small steps, as a result of which the number of possible error sources is multiplied. In particular, the regulators for the various mass flows can have different regulating deviations over time. This can lead to impermissible deviations in the stoichiometry, i.e. the ratios of the mass flows to one another. For example, a regulator can overshoot, i.e. the actual value exceeds the intended value, while another regulator brings the actual value only very slowly to the intended value, as a result of which the actual value is significantly smaller than the intended value. If such a deviation is not permissible for process-related reasons, the production plant would have to be shut down when the ratios of the actual values of the reactants are outside prescribed intervals.

Although a possible solution is, in the case of relatively large deviations in the desired ratio of the flow rate to the materials fed in relation to one another, which are nevertheless still within particular limit values, to interrupt the further increase in the flow rate of the prescribed material until the system has stabilized again. This procedure has various disadvantages:

The slow increase in flow rate of the output material means a loss of production.

There is an increased requirement for monitoring by operating personnel during such critical phases.

The procedure described is complex and has only a small error tolerance.

Furthermore, provision of relatively large volumes of intermediate storages for some of the participating materials can be needed. In the example of the production plant shown in FIG. 1, it can, for instance, be necessary, for the purpose of start-up, to keep a relatively large amount of the two coproducts (i.e. the intermediate Z2 and the second output material A2) at the ready in an intermediate storage. This is, at least when it extends over a relatively long period of time, economically disadvantageous and incurs safety risks. This leads to increased capital and maintenance costs. In addition, it is quite possible to conceive of cases in which such a procedure is subjected to limits purely for technical reasons, for instance when one of the coproducts is stable for only a limited time or attacks materials of the intermediate storage on prolonged storage.

However, these particular challenges in relation to the operation of chemical production plants for coupled reactions have hitherto been accorded limited attention in the relevant patent and technical literature. In relation to the production of dinitrotoluene by the coupled reactions nitration of toluene to form mononitrotoluene (e.g. chemical reaction C1 in FIG. 1) and nitration of mononitrotoluene to form dinitrotoluene (e.g. chemical reaction C2 in FIG. 1), the ratios of the individual mass flows have frequently been discussed in the patent literature, but without acknowledging the abovementioned problems in particular. ACS Symposium Series, Vol. 623, chapter 21, "Industrial Nitration of Toluene to Dinitrotoluene", discloses merely in a quite general way that the inflows of raw materials have to be monitored precisely and emergency shutdowns are provided in particular cases for safety reasons.

SUMMARY

It is therefore an object of the present invention to provide an improved process for the continuous production of a product via at least two coupled chemical reactions.

The object of the invention is achieved by a process as claimed in claim 1; preferred embodiments can be derived from the dependent claims and the description below.

According to the invention, a process for the continuous production of a product via at least two coupled chemical reactions is provided. At least two starting materials are fed to a first chemical reaction, a plurality of intermediates is produced from the starting materials by the first chemical reaction and at least one of the intermediates is fed to a second chemical reaction. The at least one intermediate fed to the second chemical reaction is processed further in a second chemical reaction, in particular using at least one further material, to give a plurality of output materials, namely to form the chemical product and at least one further output material. The flow rates of the materials introduced, which are fed to one of the reactions, are set by means of a respective regulating device, with a separate regulating device being assigned to each of the materials fed in and at least one of the regulating devices, in particular all of the regulating devices, being in each case supplied with a control variable prescribed by a regulator. For the present purposes, regulating devices are devices which can alter a physical parameter, e.g. a mass flow, as a function of an input variable, e.g. the output of a regulator. These include, for example, valves whose degree of opening can be adjusted or pumps for which the amount conveyed can be adjusted.

The process of the invention is characterized in that, to change the production rate of the chemical product, at least one of these regulating devices is supplied during a settling-down phase in each case with a temporary control variable instead of the control variables prescribed by the respective regulators, where the temporary control variable or the temporary control variables are generated as a function of a prescribed value from at least one control unit.

For the purposes of the present invention, two chemical reactions are coupled when at least one coproduct of a chemical reaction is, optionally after treatment, used as reactant in the other chemical reaction. Here, a coproduct of a chemical reaction is a product which is inevitably formed in addition to the desired target product of the reaction as a result of the natural stoichiometry of the underlying reaction equation. In the case of the preparation of dinitrotoluene, this coproduct is the water which is formed during the nitration reaction and is taken up by the sulfuric acid. This is to be distinguished from by-products whose formation can at least be minimized by improved reaction conditions, suitable selection of the catalyst and like measures.

DETAILED DESCRIPTION

Figure 1:
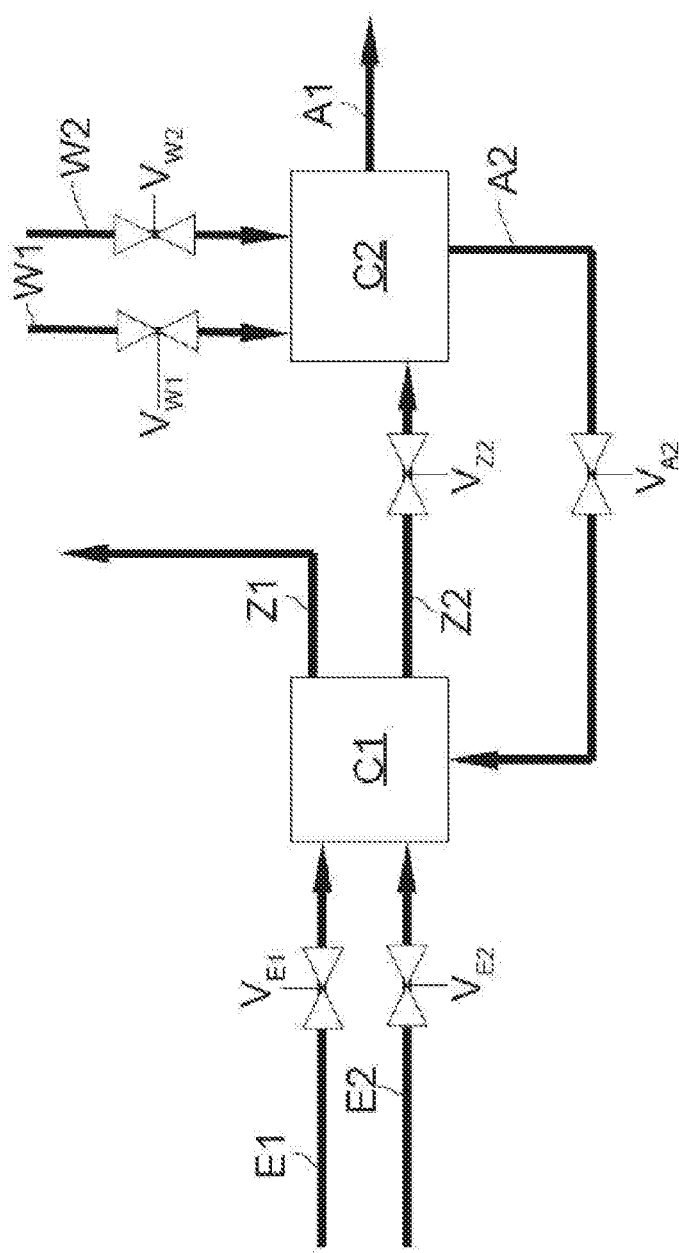
FIG. 1 is a process flow diagram of a conventional process for the continuous production of a chemical product.

The process claimed here consequently relates to carrying out a change in the production rate. For the purposes of the present invention, the production rate is, in particular, a desired flow rate, i.e. the intended value of the flow rate, of a material participating in the process. In particular, this can also be applied in the case of a change, in particular an increase, in the production rate by at least 30%, preferably at least 50% and in particular during running-up of a production plant from the rest state.

In a starting state, the production rate has a different value than in a final state. In particular, the process can be employed in running up the production process; then, the production rate in the starting state is 0 and in the final state the production rate, in particular the nominal capacity of a production plant, is different from 0. As an alternative, the production plant can be operated, for instance for reasons of demand, for a particular period of time at only a reduced capacity, for example at half the nominal capacity, and should then be run up as quickly as possible back to the nominal capacity. The converse case of a significant reduction in the current production capacity is likewise encompassed by the process of the invention.

The key aspect of the invention is then, in particular, that, in order to change the production rate, the regulators (i.e. at least one of the regulators) are temporarily taken out of action and replaced by one or more controls. The control then generates the control variables on the basis of a prescribed value. The prescribed value is, in particular, related to the change in the production rate. The prescribed value can be, in particular, the intended value of the flow rate of a material which is fed to one of the chemical reactions; as an alternative, the prescribed value can be the intended value of the flow rate of an output material which is supplied by a chemical reaction.

When exactly one regulating device is supplied with such a temporary control variable during the settling-down phase, this is preferably a regulating device by means of which the flow rate of a material (in particular a starting material) which is fed to one of the chemical reactions is set. The user setting is then preferably the intended value of the flow of this material. In the case of the preparation of dinitrotoluene, the new intended value of the flow rate of toluene preferably represents the user setting.

The procedure according to the invention makes it possible to achieve a sudden change, in particular increase, in the actual values of the flow rates of the individual materials, which after only a few seconds reach values which are quite close to the flow rates of the steady state to be achieved. The bridging of the control variables supplied by the regulator by the temporary control variables enables each regulator to settle down on its own without the regulators having any influence on the process. This settling-down process has the advantage that the actual values very quickly reach a steady state as a result of the provision of the temporary control variables; since the intended values of some regulating circuits in such a nested production process generally depend on (now steady-state) actual values of other regulating circuits, the settling down is aided.

In a preferred embodiment, all regulating devices can be supplied with control variables in this way as well. This can further accelerate the settling-down process.

The control variables are preferably generated by means of at least one control function of the control unit with the aid of a database in which mathematical relationships between a temporary flow rate and an associated control variable are stored for each of these regulating devices. The control unit thus makes use during the settling-down phase of previous knowledge, for example of the type "When the valve has been turned open to such an extent (control variable), then a particular amount of material (flow rate) flows through this valve".

This relationship makes it possible for the control unit to set the valve sufficiently well to a desired intended value, without it being important in this phase that the actual value of the flow rate corresponds exactly to the intended value. Rather, it is of importance in this settling-down phase to bring the process at a high level firstly to a steady state. As a result of the essentially simultaneous adjustment of all relevant regulating devices corresponding to the expected flow rates, such a steady state can be reached within a very short time, in particular within a few seconds.

Preferably, the intended value of a temporary flow rate is generated for each of the materials fed in taking into account the prescribed value, in particular with the aid of a stoichiometric function, and this intended value is used as a basis for generating the associated temporary control variable. As in steady-state regulated operation, the flow rates of the materials fed in have to be matched to one another to at least some extent during the settling-down phase so that the regulators have the opportunity of settling down. The stoichiometric function generates mutually suitable intended values of the flow rates of the individual materials, corresponding to the ratio of amounts required by the chemical reactions. The stoichiometric function can here make recourse to further measured values of the process, in particular to values which allow conclusions as to the concentration of the materials, for example the density.

After a settling-down phase has concluded, a change is preferably made from supplying these regulating devices with the temporary control variables to supplying them with the control variables prescribed by the respective regulators.

When the regulators have settled down, they assume the provision of control variables again. Since the difference between the actual values and the intended values (of the regulators) of the flow rates is now quite small, the regulating difference still present can be corrected without problems by the individual regulating circuits.

The conclusion of the settling-down phase so that the provision of the control variables can be changed over is preferably achieved when all regulators supply a control variable whose ranges of fluctuation are below prescribed threshold values.

The process is particularly suitable for preparing dinitrotoluene, which will be explained in more detail with the aid of the working example.

The invention further relates to the use of a chemical production plant for carrying out the process of the invention.

The invention further relates to a regulating and control arrangement which is configured for regulating and controlling the process of the abovementioned type. The arrangement comprises a control unit and a plurality of regulators for the varying supply of a control variable to regulating devices for influencing the flow rate of a flowing material, a database for storing relationships between control variables and flow rates, with the aid of which the control unit supplies temporary control variables as a function of intended values of the flow rates.

Figure 2:
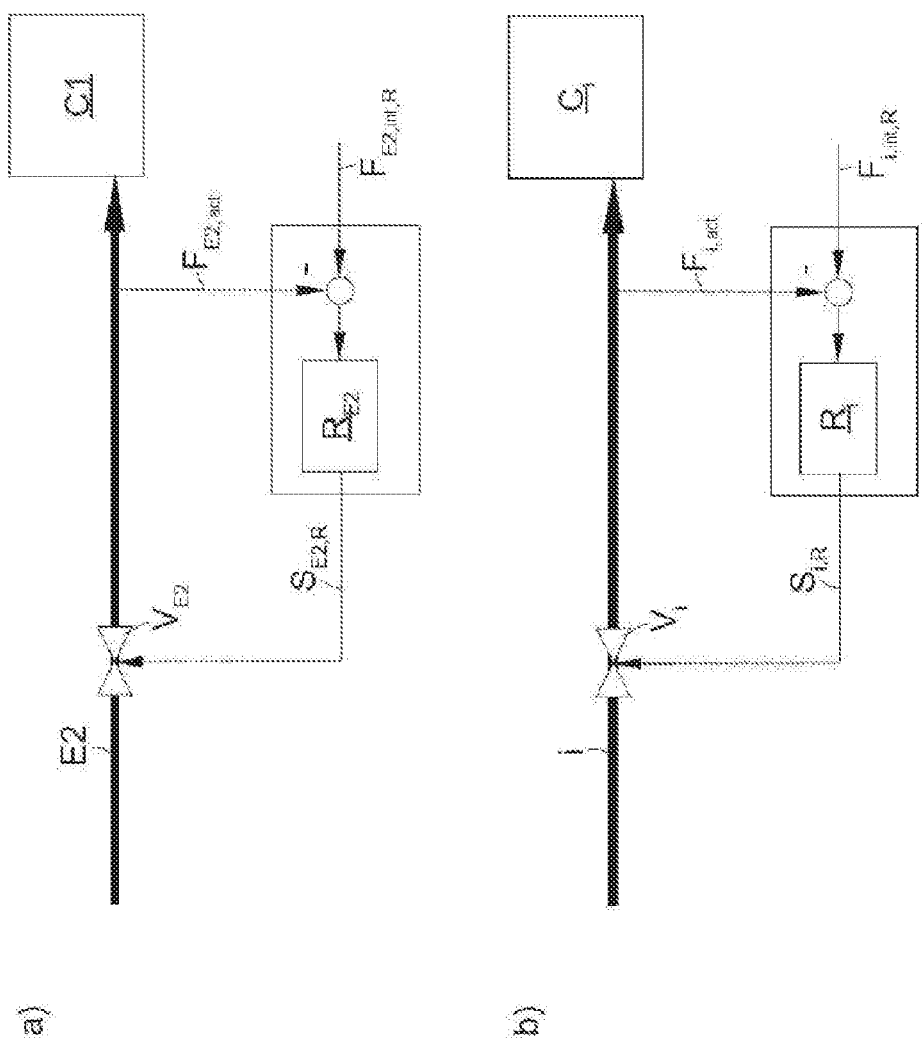
FIG. 2 shows two process flow diagrams to illustrate the regulation of the mass flows in the process corresponding to FIG. 1.
Figure 3:
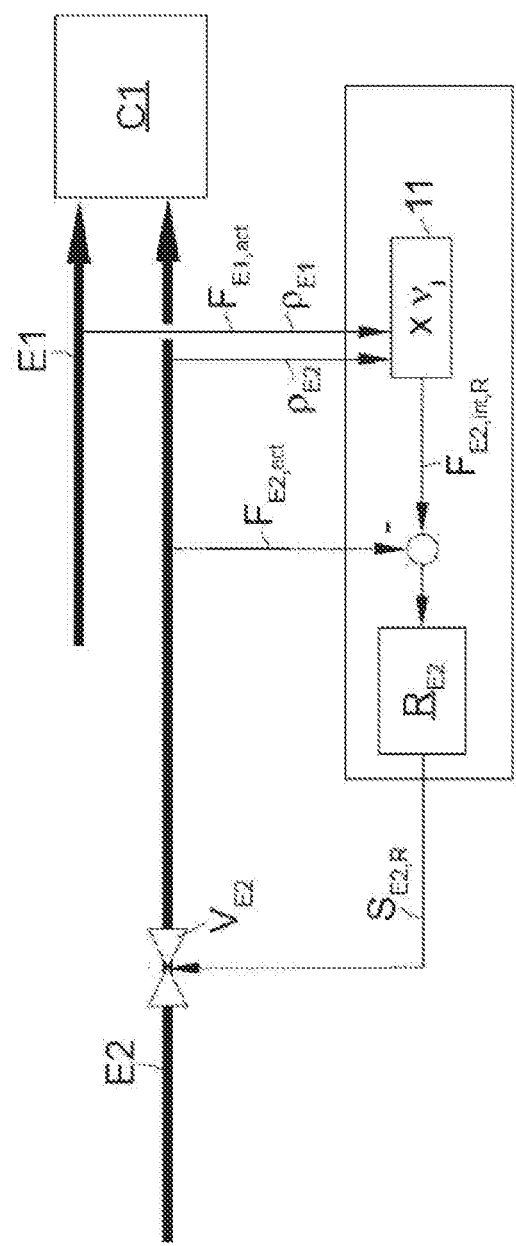
FIG. 3 is the process flow diagram of FIG. 2a supplemented by a computer unit for determining intended values.
Figure 4:
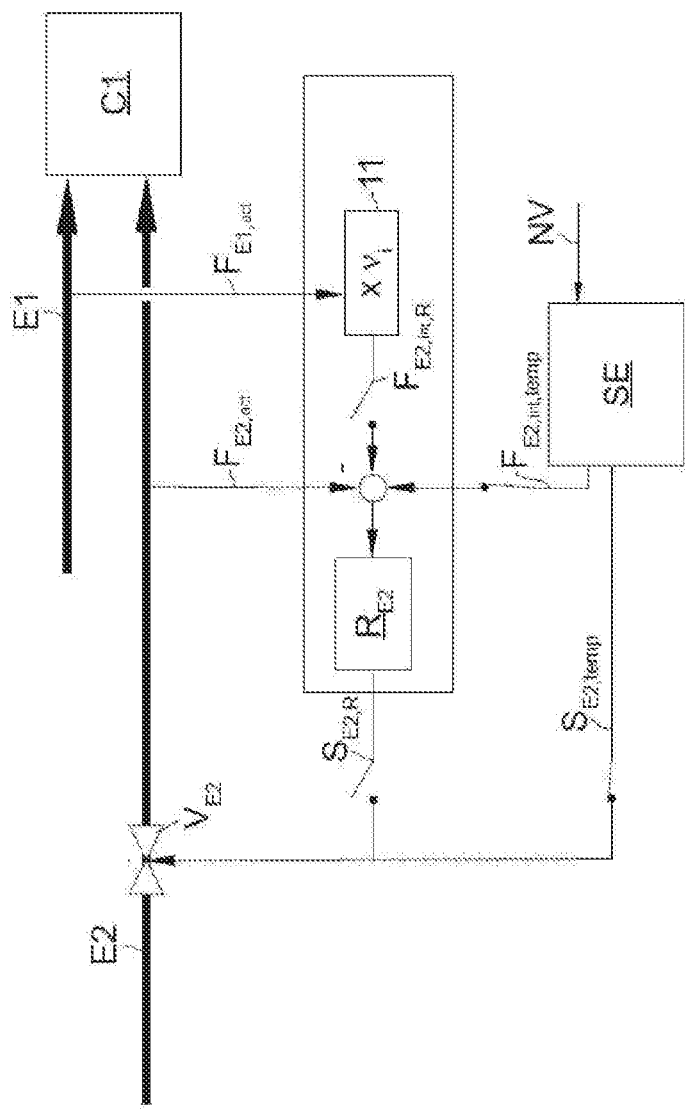
FIG. 4 is the process flow diagram of FIG. 3 supplemented by a control unit for generating temporary control variables and intended values.
Figure 5:
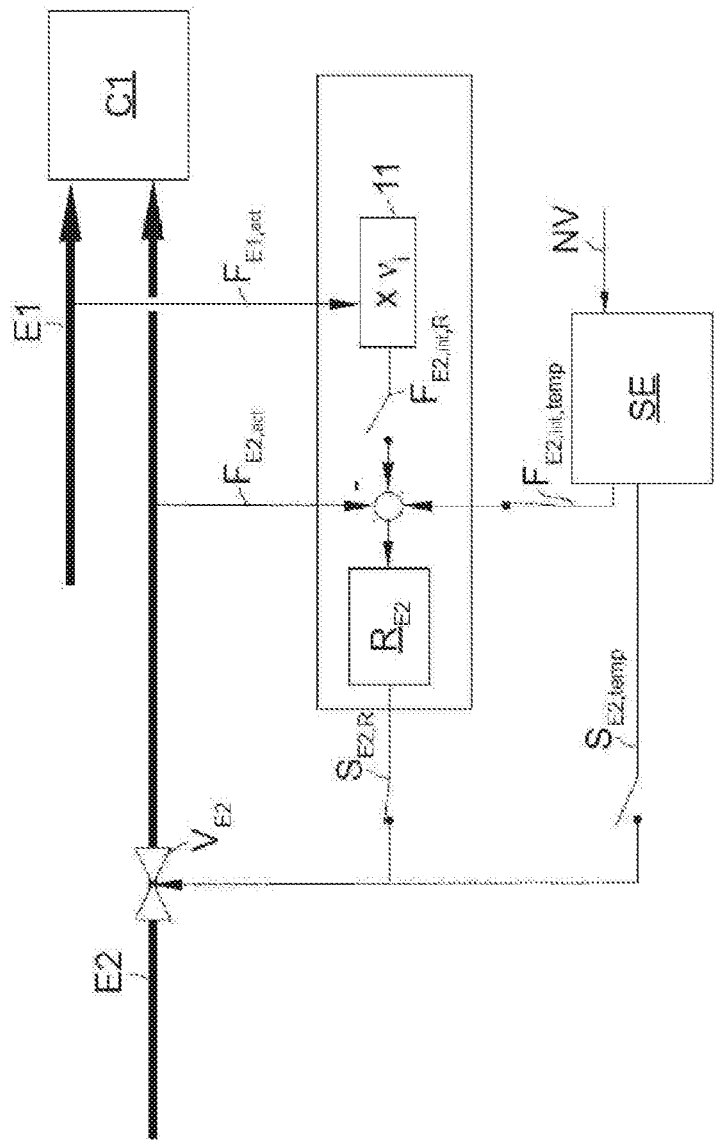
FIG. 5 is the process flow diagram of FIG. 4 in a subsequent process step.
Figure 6:
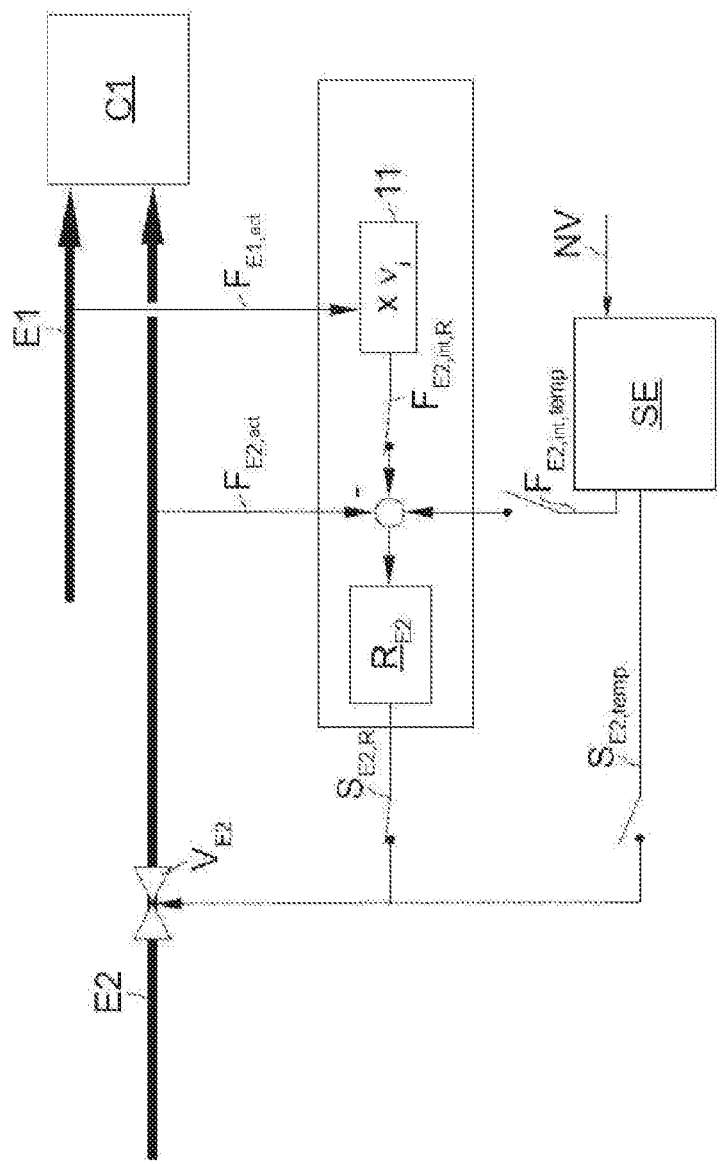
FIG. 6 is the process flow diagram of FIG. 5 in a subsequent process step.
Figure 7:
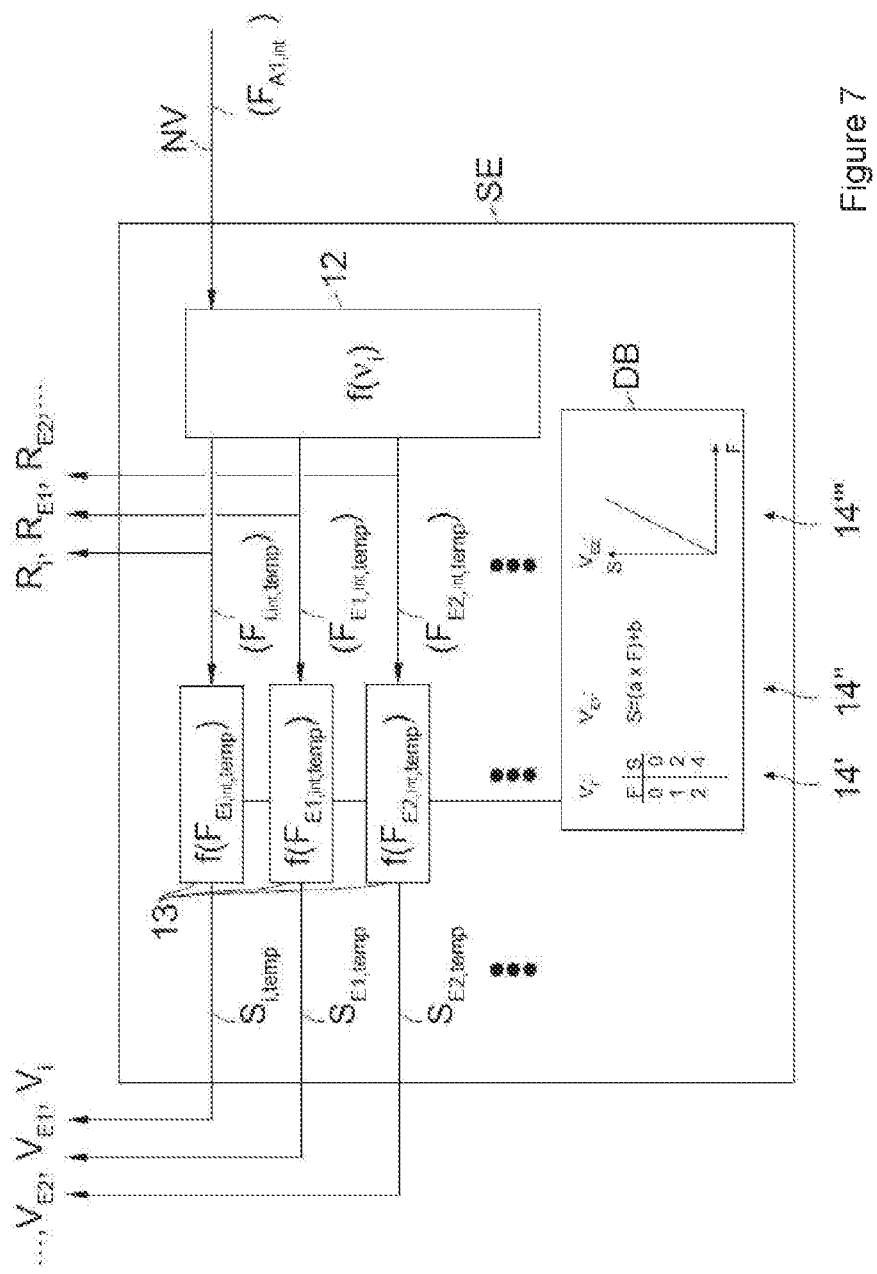
FIG. 7 is the control unit of FIGS. 4 to 6 in detail.
Figure 8:
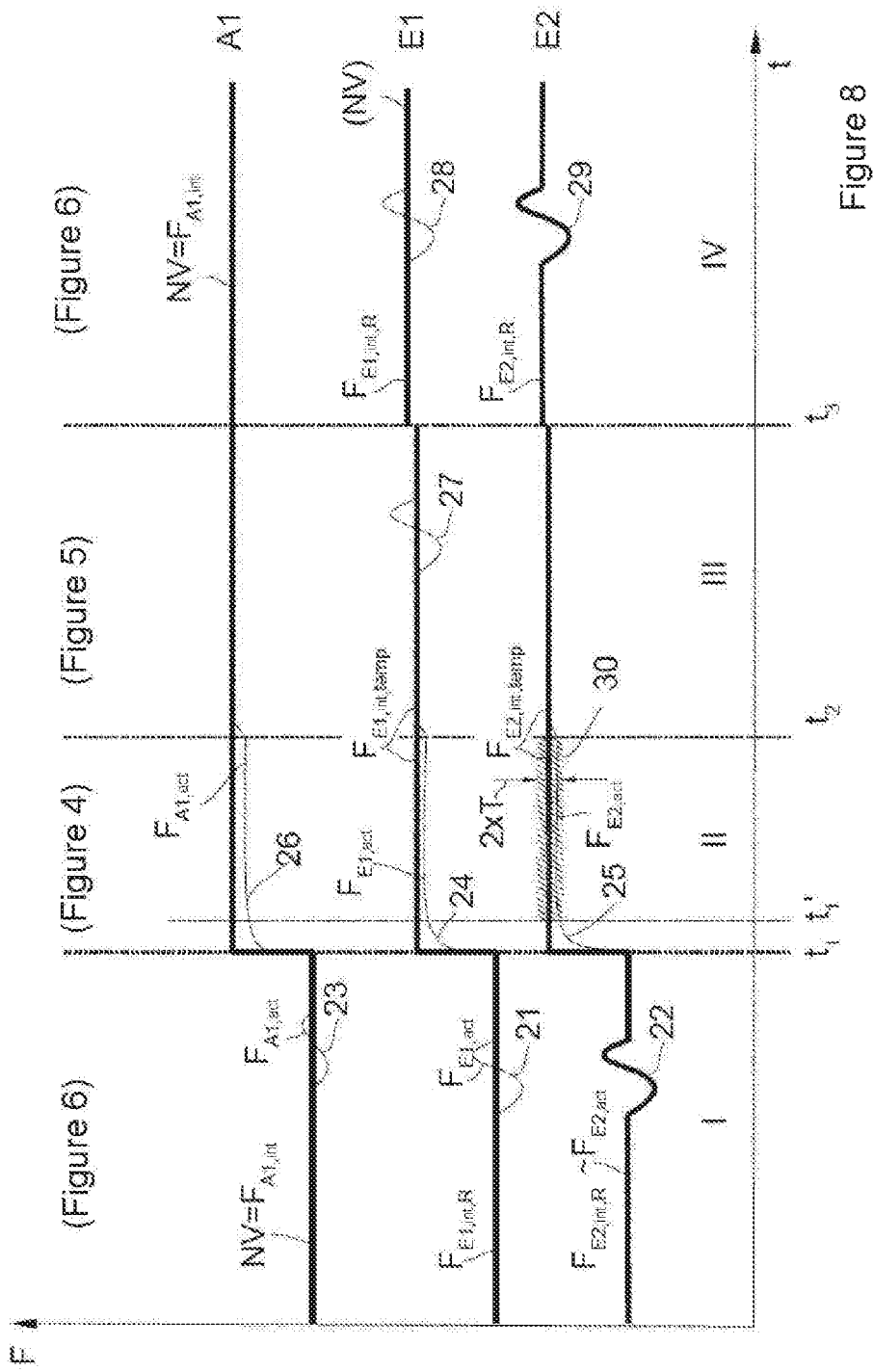
FIG. 8 is a graph showing flow values while carrying out the process of the invention.
Figure 9:
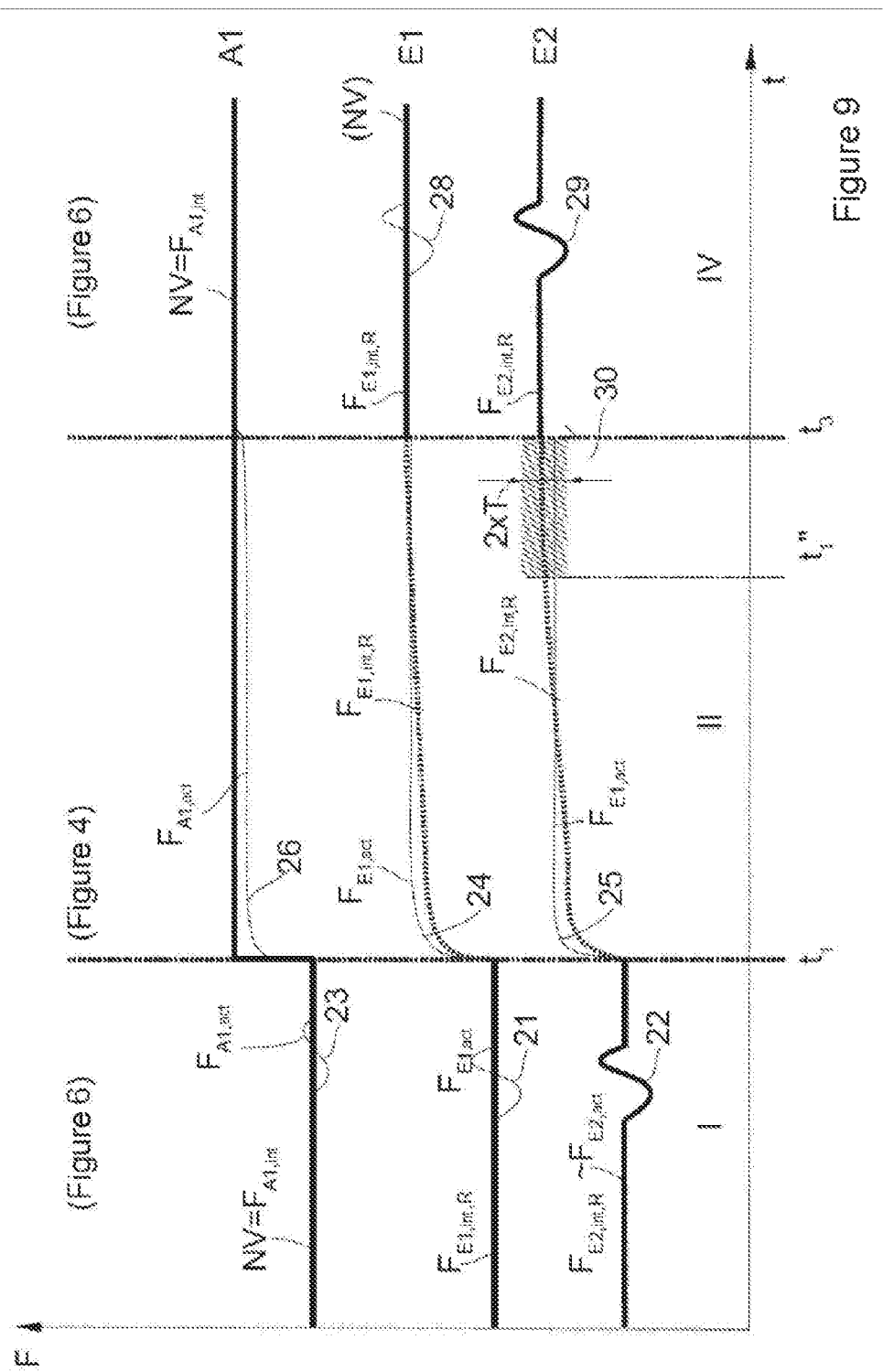
FIG. 9 is a graph showing flow values while carrying out an alternative process according to the invention.
Figure 10:
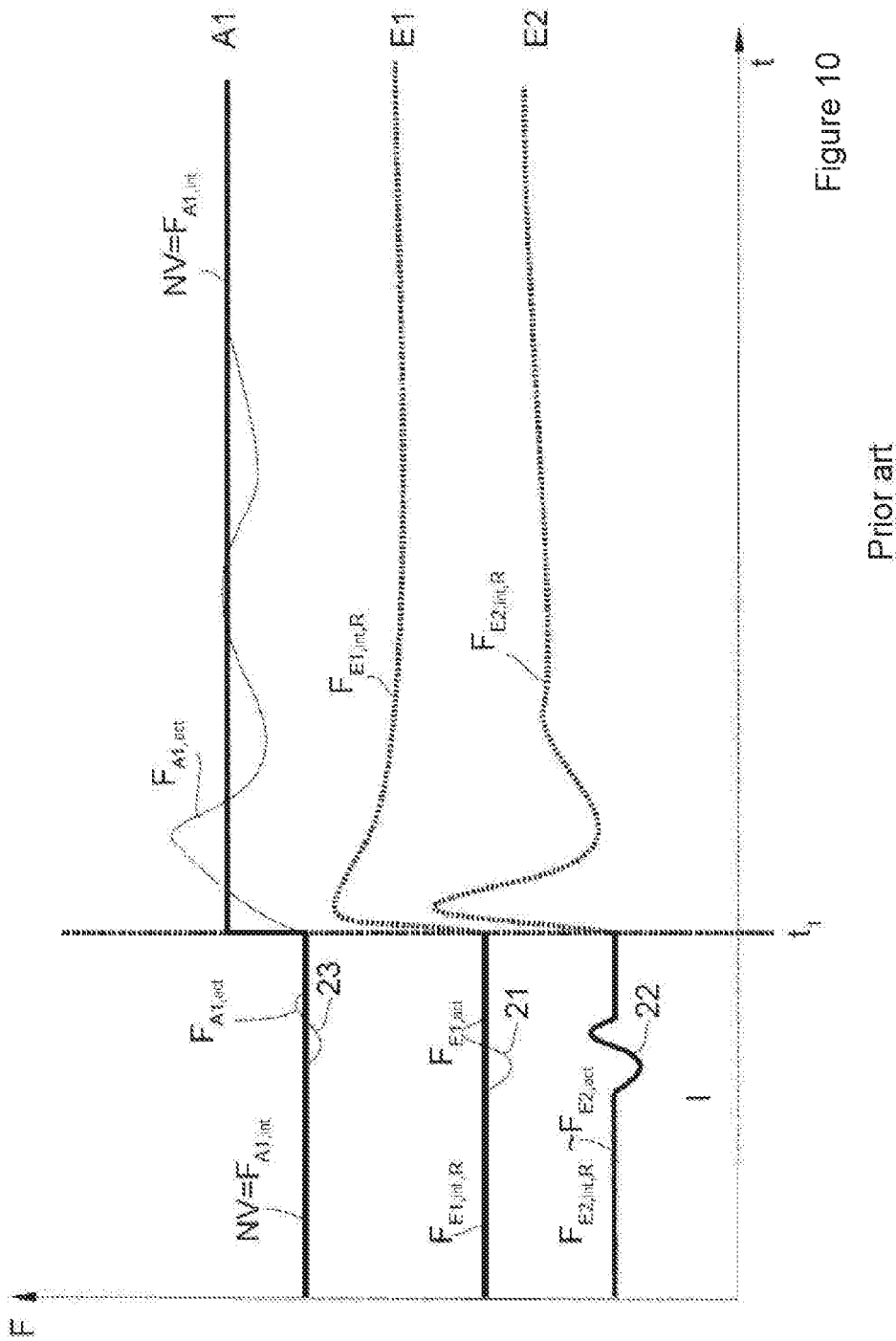
FIG. 10 is a graph showing flow values while carrying out a process according to the prior art.

The invention is illustrated below with the aid of the figures, which show:

FIG. 1 a process flow diagram of a conventional process for the continuous production of a chemical product;

FIG. 2 two process flow diagrams to illustrate the regulation of the mass flows in the process corresponding to FIG. 1;

FIG. 3 the process flow diagram of FIG. 2a supplemented by a computer unit for determining intended values;

FIG. 4 the process flow diagram of FIG. 3 supplemented by a control unit for generating temporary control variables and intended values;

FIG. 5 the process flow diagram of FIG. 4 in a subsequent process step;

FIG. 6 the process flow diagram of FIG. 5 in a subsequent process step;

FIG. 7 the control unit of FIGS. 4 to 6 in detail;

FIG. 8 a graph showing flow values while carrying out the process of the invention;

FIG. 9 a graph showing flow values while carrying out an alternative process according to the invention;

FIG. 10 a graph showing flow values while carrying out a process according to the prior art.

FIG. 1 schematically shows a process flow diagram of a process for the continuous production of a chemical product. The chemical product to be produced is in this example a first output material A1.

At least two starting materials E1, E2 are used and are fed to a first chemical reaction C1. The flow rate (in the further course of the description denoted by the reference symbol F) of the respective starting materials E1, E2 introduced is set by means of regulating devices $V_{E1}$, $V_{E2}$ for example flow valves. In the first chemical reaction C1, the starting materials E1, E2 are processed to give a plurality of intermediates, in the present case two intermediates Z1, Z2.

One of the intermediates, here the second intermediate Z2, is fed directly to a second chemical reaction C2. The flow rate of the second intermediate Z2 is set by means of a regulating device $V_{Z2}$. In addition, further materials W1, W2 are fed to the second chemical reaction C2. The flow rates of the further materials are also set by means of regulating devices $V_{W1}$, $V_{W2}$. One of the further materials W1, W2 can in turn be produced by working up from the first intermediate Z1.

The second chemical reaction C2 then processes the materials W1, W2 fed thereto to give the two output materials A1, A2. While the first output material A1 represents the chemical product which is ultimately to be produced, the second output material A2 is fed back to the first chemical reaction C1. This can occur directly, as shown in FIG. 1; as an alternative, the second output material A2 can also be mixed with one of the other starting materials before introduction into the first chemical reaction (not shown).

The exceptional feature and at the same time the difficulty in carrying out such processes is that at least one material (A2, Z2) which is produced only in one of the preceding chemical reactions C2 or C1 is in each case fed to the chemical reactions C1 and/or C2. Thus, when the production rate of a chemical reaction, for example of the second chemical reaction C2 for the ultimate production of the first output material A1 is to be increased, for example doubled, it is absolutely necessary for the material Z2 fed thereto (and also the other materials) to be provided at a correspondingly increased production rate of the first chemical reaction C1.

In addition, in the present case the first chemical reaction C1 requires the second output material A2 likewise as a material to be fed in, with the second starting material A2 being produced only by the second chemical reaction C2. There is consequently a back-coupling, so that each of the chemical reactions C1, C2 is dependent on the products of the respective other chemical reaction C2, C1.

Owing to, for example, wear in the regulating devices and changes in the command variables, the actual flow rates of the materials are always subject to fluctuations which are tolerable within prescribed limits (including limit value intervals). Such limit values can be prescribed by automatic or manual input of or changes in parameters, in particular by means of further regulating building blocks, e.g. level regulators. Limit values can be provided for deviations of redundant flow measurements of the same stream or deviations between intended and actual values of the flow rates of individual streams. The permissible limit values can be set down differently for each material. An increased amount of sulfuric acid is, for example in the nitration of toluene, less damaging than an increased amount of nitric acid. Exceeding of such limits can in the extreme case lead to locking of the entire production plant.

Such a process is used, in particular, for producing dinitrotoluene as first output material A1. The first starting material E1 is toluene, the second starting material E2 is nitric acid, the first intermediate Z1 is a used acid (i.e. substantially diluted sulfuric acid), the second intermediate Z2 is mononitrotoluene, the second output material A2 is diluted sulfuric acid, the first further material W1 is sulfuric acid and the second further material W2 is nitric acid. In the first chemical reaction C1, nitration of toluene E1, nitric acid E2 and sulfuric acid A2 and a subsequent phase separation into mainly mononitrotoluene and mainly used acid occur. In the second chemical reaction, nitration of the mainly mononitrotoluene Z2 by means of nitric acid W2 and sulfuric acid W1 and subsequent phase separation to give dinitrotoluene A1 and mainly sulfuric acid A2 occur. The used acid Z1 originating from the first chemical reaction can be worked up, in particular concentrated up, to give the sulfuric acid W1, which is in turn fed to the second chemical reaction.

In conventional processes, this was, for example, solved by the different materials or products to be fed to a process always being kept in stock in sufficient amounts in intermediate storages. Any differences between the demand of a chemical reaction and the current production rate of the preceding chemical reaction can be equalized by means of such an intermediate storage. However, this is a rather undesirable solution to this problem, since large amounts of materials being temporarily stored also represent safety risks and/or incur high costs. There is therefore an in-principle need to keep the amount of materials subjected to intermediate storage as small as possible.

FIG. 2 illustrates how regulation of the flow rate of a material occurs. The term flow rate is used to describe the amount of a material which has flowed through, regardless of whether it is measured in mass per unit time or volume per unit time.

FIG. 2a illustrates the regulation of flow for the example of the second starting material E2. The second starting material 2 is to be fed at a particular flow rate $F_{E2,int,R}$ to the first chemical reaction C1. A flow measuring instrument which is not shown provides the actual value $F_{E2,act}$ of an instantaneous flow rate. A regulating difference is generated by comparison of this actual value $F_{E2,act}$ with the intended value $F_{E2,int,R}$. A regulator $R_{E2}$ now sends, based on this regulating difference, a control variable $S_{E,2R}$ to the regulating device $V_{E2}$ and thus supplies this regulating device with this control variable. The regulating device $V_{E2}$ then increases or reduces the actual flow rate $F_{E2,act}$ appropriately. As flow measuring instruments, it is possible to use, inter alia, ultrasonic flow measuring instruments, mass flow measuring instruments, inductive flow measuring instruments or dynamic pressure measuring instruments. Such a measuring instrument can also, unlike the depiction in FIG. 2, be arranged upstream of the regulating device $V_{E2}$. Owing to the generally higher pressure upstream of the regulating device $V_{E2}$, the actual values can be measured more reliably there since, in particular, falsification of the measured values as a result of gas phase formation is avoided. The flow measurements are preferably carried out redundantly for each flow value, in particular by carrying out a plurality of measurements at the same time.

The regulator $R_{E2}$ preferred for such applications comprises an integral component. It is preferably a PID regulator since such regulators not only regulate the instantaneous flow rate very well to the intended value but can also precisely regulate the total amount of material which has flowed through in the long term.

FIG. 2b is essentially a copy of the regulating circuit depicted in FIG. 2a. However, as a difference from the depiction in FIG. 2, general reference symbols have been used in order to make it clear that the regulating circuit depicted in FIG. 2a can also be employed for regulating the flow of all other materials introduced, i.e. the other starting material E1, the further materials W1, W2, the second intermediate Z2 and the second output material A2, which each have to be fed in regulated amounts to the two chemical reactions. Basically, the index i thus represents the materials E1, E2, W1, W2, Z2, A2, whose respective flow rates $F_i$ are to be regulated.

In steady-state regulated operation, the production rate of the output material is substantially constant. The chemical reactions are then operated at substantially constant production rates. This means that the chemical reactions have to be supplied with a substantially constant inflow of appropriate materials. For this, it is necessary that the flow rates of all materials be regulated. FIG. 3 now shows, for the example of the material E2, how the flow rate thereof $F_{E2,act}$ is regulated as a function of the flow rate of another material (by way of example the instantaneous flow rate $F_{E1,act}$ of the other starting material E1).

The actual value $F_{E1,act}$ of the flow rate of the other starting material E1 is measured by the flow measuring instrument (not shown) and fed into a computer unit 11. This computer unit 11 then calculates the necessary flow rate for the second starting material E2, which corresponds to the intended value $F_{E2,int,R}$ of the flow rate, in a manner analogous to FIG. 2a. This calculation is carried out taking into account the stoichiometric conditions within the first chemical reaction C1. In FIG. 3, this is indicated in simplified form by multiplication of the stoichiometric coefficient $v_i$ by the actual value $F_{E1,act}$ of the flow rate of the other starting material E1. Should there be fluctuations in the flow rate $F_{E1,act}$ of the first starting material E1, these deviations in the flow rate are briefly also reflected by the regulating circuit, taking into account the stoichiometric coefficient, onto the intended value of the flow rate $F_{E2,int}$ of the second starting material E2 (see reference symbols 21, 22 and 28, 29 in FIG. 8 below). The actual flow rate $F_{E2,act}$ of the second starting material E2 then follows the actual flow rate $F_{E1,act}$ of the first starting material E1. The flow rate of the first starting material E1 can in turn be regulated as a function of the flow rate of another material participating in the production process, in particular with the aid of a desired output $F_{A1,int}$ of the first output material A1.

The calculation of the intended values by the computer unit 11 can also be carried out employing further chemical and/or physical parameters. It is shown that the respective density $\rho_{E1}$ and $\rho_{E2}$ is determined for the streams of the materials E1 and E2 and supplied to the computer unit 11. The concentration of the respective materials can be calculated from the density, which is significant for the required flow rate. In the preparation of dinitrotoluene, which is described in more detail below, proportions of dinitrotoluene in the second intermediate can be determined with the aid of the density. The addition of nitric acid (second further material W2) can correspondingly be reduced, the greater the proportion of dinitrotoluene in the second intermediate Z2. These explanations imply that the products designated as materials here do not have to be pure materials.

The measures which have to be carried out to effect a sudden increase in the production rate will now be explained with the aid of FIGS. 4 to 7. This process is employed particularly when the production of the output material is to be resumed again after the plant has been down. The representation of the density ρ of the materials E1 and E2 will be omitted in the further figures for reasons of clarity.

FIG. 4 is based on the regulating circuit shown in FIG. 3. However, it can be seen that the data connection between the regulator $R_{E2}$ and the regulating device $V_{E2}$ has been interrupted. This means that the regulating device $V_{E2}$ is not supplied with the control variable $S_{E2,R}$ of the regulator $R_{E2}$ prescribed by the regulating circuit. Instead, the regulating device $V_{E2}$ is supplied with a temporary control variable $S_{E2,temp}$ which is provided by a control unit SE. Consequently, the control variable $S_{E2,R}$ provided by the regulator is overwritten by the temporary control variable $S_{E2,temp}$ provided by the control unit SE. The calculation of the temporary control variable $S_{E2,temp}$ is in turn based on an input value to the control unit SE, for example a user setting NV which is, for example, a desired intended value for the production rate of the first starting material A1. The calculation of this is explained further below with the aid of FIG. 7.

At the same time, a temporary intended value $F_{E2,int,temp}$ of the flow rate of the second starting material E2 is also provided by the control unit SE and is supplied to the regulator $R_{E2}$. The regulator $R_{E2}$ is consequently operated in a type of idle mode in which a control variable $S_{E2,R}$ is provided or generated by the regulator $R_{E2}$ but this control variable $S_{E2,R}$ is not (yet) supplied to the regulating device $V_{E2}$. The exceptional feature here is also that the regulator $R_{E2}$ does not work on the basis of the intended value $F_{E2,int,R}$ which is prescribed by the process, but instead works on the basis of the intended value $F_{E2,int,temp}$ which is provided by the control unit SE, which will likewise be explained in more detail below.

In a second step, the regulating device $V_{E2}$ is, as shown in FIG. 5, then no longer supplied with the temporary control variable $S_{E2,temp}$ but instead with the control variable $S_{E2,R}$ provided by the regulator $R_{E2}$. The exceptional feature that the regulator $R_{E2}$ is still supplied with the intended value $F_{E2,int,temp}$ by the control unit SE without the flow rates of other materials being taken into account is, however, maintained.

In a third step, as shown in FIG. 6, the intended value entered into the regulator $R_{E2}$ is then also changed over to the intended value $F_{E2,int,R}$ prescribed by the process; all values prescribed by the control unit SE, namely the intended value $F_{E2,int,temp}$ and the control variable $S_{E2,temp}$, are again disregarded as of now. This then corresponds essentially to the circuit design of FIG. 3, since the process is now completely decoupled from the control unit SE.

The mode of operation of the control unit SE, as is shown in FIGS. 4 to 6, will now be explained in more detail with the aid of FIG. 7. The user setting NV can be seen as input value at the right-hand side. The user setting can be, for example, a desired production rate $F_{A1,int}$ of the product A1 to be produced. When the amount of this product which is to be produced is known, the required intended values for all materials participating in the process can be calculated on the basis of the stoichiometric conditions (and in particular with inclusion of further physical or chemical parameters of the materials), which is carried out by the functional block 12. Output values from this functional block 12 are then the temporary intended values $F_{i,int,temp}$, for each of the significant materials whose flow rates are regulated in the process. The intended values $F_{E1,int,temp}$, $F_{E2,int,temp}$ of the flow rates of the two starting materials are shown by way of example and as representative of other materials. This also applies analogously for the intermediate Z2 and the further materials W1, W2. The functional block 12 also uses, in a manner analogous to the computer unit 11 (FIG. 3), further chemical and/or physical parameters for determining the intended values, for example values, in particular the density p, which allow conclusions to be drawn in respect of the concentration of the individual materials.

These temporarily prescribed intended values $F_{i,int,temp}$, $F_{E1,int,temp}$, $F_{E2,int,temp}$ are then each transmitted to a control function 13. The control function 13 in each case calculates, on the basis of the prescribed temporary intended value $F_{i,int,temp}$, $F_{E1,int,temp}$, $F_{E2,int,temp}$ of the flow rate, a temporary control variable $S_{i,temp}$, $S_{E1,temp}$, $S_{E2,temp}$ for all relevant regulating devices $V_i$ by means of which the flow rates of the significant materials can be set. However, the temporary control parameters are not regulated-in, as is otherwise customary; rather, the control variables are generated with the aid of a database DB in which many control variables or calculation parameters for calculating such control variables are stored.

Such a database DB is outlined by way of example in FIG. 7. Thus, a relationship table 14' with flow values F and the associated regulating variables S is shown by way of example for the regulating device $V_i$. Should, for example, the flow value be 0, the control variable 0 is to be provided; in the case of a flow rate of 1 to be set, the control variable 2 is to be provided, and in the case of a flow rate to be set of 2, the control variable 4 is to be provided. A corresponding situation also applies to all further relevant regulating devices. Intermediate values can be calculated by interpolation. Such a mathematical relationship does not have to be present in tabular form; it is also possible for calculation formulae 14'' or sets of characteristic data 14''' to be stored and then to be evaluated mathematically. These relationships 14 can be generated by experimental determination or an engineering calculation.

Such relationships 14 do not necessarily have to be stored statically, but can instead be updated dynamically. For this purpose, current actual values can be compared with current control variables; on the basis of this, updating of the relationships stored in the database DB can be carried out.

The relationships can additionally encompass further dependences. Thus, a pump is used in the process for conveying a material which is also required in another production process. Depending on the loading of the pump, pressure differences can arise in the feed conduit for a material, which necessitates a dependence of the control variable not only on the intended flow rate but also on the pressure in the conduit.

In a manner analogous to the sudden change in the production rate and the associated change in the flow rates, the regulation of the coolant stream can also be changed over from temperature regulation to a control. The required relationships can likewise be stored in the database DB.

The process of the invention will be illustrated still further with the aid of the graph in FIG. 8. Curves for the different flow rates F for, by way of example, the materials A1 (first output material), E1 (first starting material) and E2 (second starting material) can be seen. Here, the bold line always represents the relevant corresponding intended value $F_{A1,\ldots,int}$, $F_{E1,\ldots,int}$ or $F_{E2,\ldots,int}$. If the respective actual value $F_{A1,act}$, $F_{E1,act}$ or $F_{E2,act}$ has been regulated-in well, the actual value coincides with the respective intended value and cannot be explicitly seen in FIG. 8. However, should there be a difference between the actual value and the associated intended value, the curves of the respective actual values are shown in FIG. 8 as thin lines which are provided with the reference symbols 21-30.

Different time ranges, namely the time range I ($t<t_1$), the time range II ($t_1<t<t_2$), the time range III ($t_2<t<t_3$) and the time range IV ($t>t_3$), are shown in FIG. 8.

In the time range I, the process operates in a steady state, as is shown in FIG. 6 (or in FIG. 3). The user setting NV corresponds to the intended value $F_{A1,int}$, i.e. the desired flow rate for the first output material A1. Taking into account the stoichiometric ratios, an intended value $F_{E1,int,R}$ is prescribed for the flow rate of the first starting material E1, which is entered into the corresponding regulator. The intended value $F_{E2,int,R}$ for the flow rate of the second starting material E2 is dependent on the actual value $F_{E1,act}$ of the flow rate of the first starting material E1. Thus, a fluctuation of the actual value $F_{E1,act}$ of the flow rate of the first starting material E1 denoted by way of example by the reference symbol 21 in the time range I. The intended value $F_{E2,int,R}$ for the flow rate on the second starting material follows the actual value $F_{E1,act}$ of the flow rate of the first starting material E1, which can be seen from the correspondingly shaped fluctuation indicated by the reference symbol 22. In the case of a well adjusted regulator, the actual value $F_{E2,act}$ of the flow rate of the second starting material E2 follows the corresponding intended value $F_{E2,int,R}$, so that the actual curve (not explicitly visible) coincides with the intended curve (shown here in bold).

At the point in time $t_1$ the intended value for the desired flow rate $F_{A1,int}$ is increased suddenly by means of the user setting NV, for example by 50%. The regulators are taken out of action for this purpose, as shown in FIG. 4. Instead, the temporary control variables $S_{E1,temp}$ and $S_{E2,temp}$ (see FIG. 4) are supplied directly to the regulating devices $V_{E1}$, $V_{E2}$. At the same time, the temporary intended values $F_{E1,int,temp}$ and $F_{E2,int,temp}$ are provided to the regulators by the control unit SE, which results in the formation of a step in the intended value curves at the point in time $t_1$ in FIG. 8.

The different regulating sections for the individual materials then react differently to the correspondingly changed sudden intended value provision or the control variable change. It is common to all three actual values in the time range II that they are not regulated specifically to an intended value but are only guided on the basis of values derived from experience, which are stored in the database DB (FIG. 7).

In this respect, it is no surprise that at the point in time $t_2$ the flow rates $F_{A1,act}$, $F_{E1,act}$, $F_{E2,act}$ are not regulated exactly to the associated intended value. However, it can be seen that, owing to the control exerted according to the invention, the actual values of the flow rates are quite close to the intended values and a steady state has been established at the point in time $t_1'$ (a few seconds after $t_1$). At the point in time $t_2$, the change is then made from the temporary control variables $S_{E1,temp}$, $S_{E2,temp}$ to the control variables $S_{E1,R}$, $S_{E2,R}$, prescribed by the regulators, as shown in FIG. 5.

A tolerance bend 30 (hatched area) whose width corresponds to twice a tolerance value T is shown in FIG. 8. For a change from the temporary control variables $S_{E1,temp}$, $S_{E2,temp}$ to the control variables $S_{E1,R}$, $S_{E2,R}$ prescribed by the regulators R to be able to take place, the actual values $F_{A1,act}$, $F_{E1,act}$, $F_{E2,act}$ of the respective flow rates have to be within the tolerance band 30; the actual value must consequently not deviate from an intended value, in the present case the temporary intended value $F_{E2,int,temp}$, by more than the tolerance value T. This also applies to others of the flow quantities to be regulated; in FIG. 8, this is illustrated merely by way of example for the material E2. The tolerance band can in principle also be positioned other than centrally; the tolerance values in the upward and downward directions can differ from one another.

As an alternative or in combination, the settling-down phase can have at least one prescribed duration. This prescribed duration can have been determined in trials and stored. Should the actual value not be within the tolerance band 30 within this time, the production plant is locked, i.e. stopped, since a malfunction then has to be assumed.

In the phase III, the regulators are still supplied with the intended values $F_{E1,int,temp}$, $F_{E2,int,temp}$ which are prescribed by the control unit SE. The actual values for the starting materials E1 and E2 then very quickly attain the intended values $F_{E1,int,temp}$, $F_{E2,int,temp}$, so that the intended value curves coincide with the actual value curves shortly after the point in time $t_2$.

However, the intended values continue to be prescribed by the control unit SE, so that the individual regulating circuits cannot react to fluctuations in the flow rates of other materials. Should, for example, the actual value $F_{E1,act}$ fluctuate from the flow rate of the first starting material E1 (curve 27), this has no effect either on the intended value curve or on the actual value curve of the flow rate of the second starting material E2. In the time period II, III, i.e. between $t_1$ and $t_3$, the regulators can settle down. For this reason, the time between $t_1$ and $t_3$ is referred to as settling-down phase.

At the point in time $t_3$, the intended value supplied to the respective regulator is then also changed. The temporary intended values $F_{E1,int,temp}$, $F_{E2,int,temp}$, which are prescribed by the control unit SE, are now replaced by the intended values $F_{E1,int,R}$, $F_{E2,int,R}$ which are influenced by the process. A fluctuation in the actual value $F_{E1,act}$ of the flow rate of the first starting material E1 in the time region IV (curve 28) thus has, in a manner analogous to the time region I, a direct effect on the intended value $F_{E2,int,R}$ of the flow rate of the second starting material E1 (curve 29). No steps in the intended value curves at the point in time $t_3$ result from the change-over. The actual values are quickly brought to the new intended values by the regulating circuit which has settled down by this point in time ($t_3$).

What has been said above by way of example for the flow rates of the materials E2 and E2 applies analogously to all of the other relevant materials and flow rates.

FIG. 9 describes a further form of the process of the invention. The intended values $F_{E1,int,R}$ and $F_{E2,int,R}$ prescribed by the process are now shown for the starting materials E1 and E2 for the settling-down phase in the time range II. These are guided by other actual values of flow rates measured in the process. Since the actual values for other materials very quickly attain a steady state as a result of the procedure according to the invention, the intended values very quickly follow these actual values to a steady state.

It can be seen that the actual values $F_{E1,act}$, $F_{E2,act}$ can be closer to the intended values than the intended values $F_{E1,int,R}$, $F_{E2,int,R}$ prescribed to the regulators by the process shortly after commencement of the settling-down process $t_1$. A steady state quite close to the ultimate steady state (IV) is thus attained significantly more quickly, which assists the rapid settling-down of the regulators. This also applies to the process described in FIG. 8. There, the intended values $F_{E1,int,R}$, $F_{E2,int,R}$ prescribed by the process are not shown in the time ranges II and III for reasons of clarity.

In the alternative process corresponding to FIG. 9, the step according to FIG. 5 (time range III in FIG. 8) is now omitted entirely. Instead, the regulating devices are supplied with the temporary control variable until all regulating circuits have settled down. This is indicated by the intended values $F_{E1,int,R}$ and $F_{E2,int,R}$ having asymptotically approached a limit value. This has in each case occurred at the point in time $t_3$. The control variables supplied to the regulating devices are then changed over all at once to the control variables $S_{E1,R}$ and $S_{E1,R}$ prescribed by the regulators. The duration ($t_3$-$t_1$) of the settling-down phase II is determined by a stored value.

The monitoring of the process with the aid of limit values has already been described above; if it is found that the permissible limit values have been deviated from, the production plant is locked. In the context of the present process, the limit values can vary within different time ranges. In the time ranges I and IV, in which the plant is in steady-state operation, relatively narrow limit values are employed. In the time ranges II and III (the settling-down phase), more generous limit values are employed, i.e. larger deviations are tolerated.

A substantial advantage of the process of the invention is that the steady state of the plant associated with the new desired production quantity can be attained significantly more quickly. The period of time in which these more generous limit values have to be permitted is thus significantly shortened. Overall, the process of the invention is more reliable and produces less reject product.

The process of the invention also makes it simpler to shut down and restart the production plant when required. It is therefore more comfortable to shut down the plant for maintenance purposes. The maintenance intervals can in this way be shortened unproblematically, which increases the reliability of the plant. In addition, the control process can be supplemented by automatic flushing cycles in which the pipes are automatically flushed free of nitroaromatics, which further improves the safety of the plant.

To monitor whether the process is running correctly, it is possible to provide an indicator from which an operator can see a current stoichiometric ratio, e.g. of the first chemical reaction C1. For example, the stoichiometric coefficient of the first chemical reaction C1 between the two starting materials E1 and E2 is ν=2. The actual stoichiometric ratio can then be calculated from the actual values of the flow measurements of the two starting materials E1 and E2 taking into account the concentration of these materials. If a value of 1.9 is indicated, too little of the material E1 is being fed in, while in the case of a value of 2.1, too much of the material E1 is being fed in. Some deviation from the stoichiometric coefficient ν=2 can be intended if it is to be ensured that one of the materials is reacted. This can also be taken into account by the computer unit 11 and/or the stoichiometric function 12 in the calculation of intended values.

In FIGS. 8 and 9, the curves of the intended values of the flow rate $F_{E1,R}$ for the material E1 are provided with the reference symbol in parentheses (NV). This is intended to indicate that, in particular, the desired flow rate of the introduced toluene E1 is also suitable as user setting.

For comparison, FIG. 10 shows a process without the control according to the invention. At the point in time $t_1$, there is a step change in the user setting NV. The intended value $F_{E2,int,R}$ of the flow rate of at least the one other material E2, which is supplied to the associated regulator, is also guided by this change (taking into account the stoichiometric conditions). This flow rate overshoots. Owing to the large fluctuation in the input to this regulator, the regulator itself will become unstable. The regulator for the material E1, which is in turn dependent on the actual value $F_{E1,act}$ of the flow rate of the material E1 will accordingly fluctuate significantly more. The output rate $F_{A1,act}$ of the end product A1 will not be steady for a long time and will approach the prescribed value NV very slowly. During this time, the risk of limit values being exceeded is very high, so that an emergency shutdown is probable.

These problems have hitherto been countered by increasing the production rate $F_{A1,int}$ in small steps. The steps were selected so as to be so small (increasing the production rate by a few percentage points per step) that the individual regulating circuits could follow these changes without undesirably large fluctuations in the composition of the reaction mixture occurring. This requires a great detail of time and experienced operators. Furthermore, the output materials during this running-up fail to meet demanding requirements in terms of purity; consequently, a large amount of reject product was produced during running-up.

LIST OF REFERENCE SYMBOLS

E1, E2 Starting material
C1, C2 Chemical reactions
A1, A2 Output material
Z1, Z2 Intermediate
W1, W2, W3 Further material
Index i General index for the materials or reactions
Index act Index for actual values
Index int Index for intended values
Index temp Index for temporarily prescribed values
Index R Index for values generated by the regulating circuit
F Flow rate
R Regulator
S Control variable
V Regulating device
SE Control unit
DB Database
NV User setting
v Stoichiometric coefficient
t Time
T Tolerance value
11 Computer unit
12 Stoichiometric function
13 Control function
14 Mathematical relationship
21-29 Actual value curves which deviate from intended value curves
30 Tolerance band

The invention claimed is:

1. A process for the continuous production of a product (A1) via at least two coupled chemical reactions (C1, C2), comprising
feeding at least two starting materials comprising a first starting material (E1) and a second starting material (E2), to a first chemical reaction (C1),
thereby producing multiple intermediate materials comprising a first intermediate material (Z1) and a second intermediate material (Z2), from the at least two starting materials (E1, E2) by the first chemical reaction (C1),
feeding at least one of the intermediate materials (Z2) to a second chemical reaction (C2) and further reacting the at least one intermediate (Z2) in the second chemical reaction (C2) with at least one further material (W1, W2) to form multiple output materials comprising a first output material (A1) and a second output material (A2), wherein (A1) is a chemical product and (A2) is at least one further output material which is fed back to the first chemical reaction (C1),
wherein the flow rates ($F_i$) of the materials (E1, E2, Z2, W1, W2, A2) fed to the first chemical reaction (C1) or to the second chemical reaction (C2) are set by a respective control device ($V_{E1}$, $V_{E2}$, $V_{w1}$, $V_{w2}$, $V_{Z2}$, $V_{A2}$), with a separate control device being assigned to each of the materials fed in to the first or second chemical reaction, and at least one of the control devices being supplied with a control output ($S_{E2,R}$, $S_{i,R}$) prescribed by a controller ($R_{E2}$, $R_i$),
wherein at least one of these control devices ($V_{E2}$, $V_i$) is supplied during a stabilization phase (II, III) with a temporary control output ($S_{E2,temp}$, $S_{i,temp}$) instead of the control outputs ($SE_{2,R}$, $S_{i,R}$) prescribed by the respective controllers ($R_{E2}$, $R_i$), thereby changing the production rate of the chemical product (A1), in which the temporary control output ($S_{E2,temp}$, $S_{i,temp}$) or the temporary control outputs are generated as a function of a user setting (NV) from at least one control unit (SE).

2. The process as claimed in claim 1, wherein a control device ($V_{E2}$, $V_i$) is supplied during the stabilization phase (II, II-III) with a temporary control output ($S_{E1,temp}$, $S_{i,temp}$), in which the flow rate of a material (E1) which is fed to one of the chemical reactions (C1) is set by means of this control device ($V_{E1}$, $V_i$), wherein the user setting (NV) represents the intended value ($F_{E1,int,temp}$, $Fi_{,int,temp}$) of the flow of this material (E1).

3. The process as claimed in claim 1, wherein all control devices ($V_{E1}$, $V_{E2}$, $V_i$) are supplied with a temporary control output ($S_{E1,temp}$, $S_{E2,temp}$, $S_{i,temp}$) during the stabilization phase.

4. The process as claimed in claim 1, wherein the temporary control output ($S_{E2,temp}$, $S_{i,temp}$) or the temporary control outputs is/are generated by means of at least one control function (13) of the control unit (SE) with the aid of a database (DB), in which mathematical relationships (14) between a temporary flow rate ($F_{E2,int,temp}$, $F_{i,int,temp}$) and an associated temporary control output ($S_{E2,temp}$, $S_{i,temp}$) for each of these control devices ($V_{E2}$, $V_i$) are stored.

5. The process as claimed in claim 1, wherein a temporary intended value ($F_{E2,int,temp}$, $F_{i,int,temp}$) of a temporary flow rate is generated, taking into account the user setting (NV), for at least one material fed in to the first or second chemical reaction (E1, E2, Z2, W1, W2, A2) with the aid of stoichiometric function (12), and this temporary intended value ($F_{E2,int,temp}$, $F_{i,int,temp}$) serves as a basis for generating the associated temporary control variable ($S_{E2,temp}$, $S_{i,temp}$).

6. The process as claimed in claim 1, wherein after a stabilization phase (I; II-III) has concluded ($t_3$), a change is made from supplying the control devices ($V_{E2}$, $V_i$) with the temporary control outputs ($S_{E2,temp}$, $S_{i,temp}$) to supplying them with the control outputs ($S_{E2,R}$, $S_{i,R}$) prescribed by the respective controllers ($R_{E2}$, $R_i$).

7. The process as claimed in claim 6, wherein the conclusion of the stabilization phase ($t_3$) is reached at the earliest when all controllers ($R_i$) supply a control output ($F_{i,int,R}$) whose range of fluctuation is below a prescribed threshold value.

8. The process as claimed in claim 5, wherein the conclusion of the stabilization phase ($t_3$) is reached at the earliest when a deviation of the actual value ($F_{E2,act}$, $F_{i,act}$)

of the flow rate of the material which is set by means of the control device ($V_{E2}$, $V_i$) supplied with the temporary control output ($SE_{2,temp}$, $S_{i,temp}$) from an associated intended value ($F_{E1,int,temp}$, $F_{E2,int,temp}$, $F_{i,int,temp}$), is smaller than a prescribed tolerance value (T).

9. The process as claimed in claim 5, wherein after a first stabilization phase (II) has concluded ($t_3$), a change is made to a second stabilization phase (III), during which the at least one control device ($S_{E2}$, $S_i$) is supplied with a control output ($S_{E2,R}$, $S_{i,R}$) prescribed by the respective controller ($R_{E2}$, $R_i$), where a temporary intended value ($F_{E2,int,temp}$, $F_{i,int,temp}$) which is prescribed by the control unit (SE) serves as a basis for the controller ($R_{E2}$, $R_i$).

10. The process as claimed in claim 1, wherein the duration of the stabilization phase ($t_3$-$t_1$) is defined by a statically stored value or is determined with the aid of a statically stored mathematical relationship.

11. The process as claimed in claim 1, where the process produces dinitrotoluene (A1), wherein the first starting material (E1) comprises toluene,
the second starting material (E2) comprises nitric acid,
the first intermediate material (Z1) comprises an used acid,
the second intermediate material (Z2) comprises mononitrotoluene,
the first output material (A1) comprises dinitrotoluene,
the second output material (A2) comprises sulfuric acid, and
the at least one further material comprises a first further material (W1) comprising sulfuric acid, and a second further material (W2) comprising nitric acid,
the first chemical reaction (C1) comprises nitrating toluene (E1) with a mixture of nitric acid (E2) and sulfuric acid (A2) to form mononitrotoluene (Z2) and
the second chemical reaction comprises nitrating mononitrotoluene (Z2) with nitric acid (W2) and sulfuric acid (W1) to form dinitrotoluene (A1).

* * * * *